United States Patent [19]

Edward, Jr.

[11] 4,435,976

[45] Mar. 13, 1984

[54] APPARATUS FOR MEASURING THE HARDNESS PROPERTIES OF MATERIALS

[75] Inventor: Robert M. Edward, Jr., The Woodlands, Tex.

[73] Assignee: J B Development Corporation, The Woodlands, Tex.

[21] Appl. No.: 334,747

[22] Filed: Dec. 28, 1981

[51] Int. Cl.³ ............................................. G01N 3/44
[52] U.S. Cl. ............................................. 73/83; 73/85
[58] Field of Search ............................ 73/83, 81, 85

[56] References Cited

U.S. PATENT DOCUMENTS

| | | | |
|---|---|---|---|
| 2,790,321 | 4/1957 | Huyser | 73/83 |
| 3,877,298 | 4/1975 | Narang | 73/81 |
| 3,934,463 | 1/1976 | Venderjagt | 73/81 |
| 4,245,496 | 1/1981 | Napetschnig | 73/83 |
| 4,312,220 | 1/1982 | Borgersen et al. | 73/81 |
| 4,331,026 | 5/1982 | Howard et al. | 73/81 |

Primary Examiner—Gerald Goldberg
Assistant Examiner—John E. Chapman, Jr.
Attorney, Agent, or Firm—Bill B. Berryhill

[57] ABSTRACT

Apparatus for measuring the hardness properties of materials may comprise: a frame for supporting the apparatus and the material to be tested; a test head assembly mounted on the frame for applying predetermined measuring forces to the material and a clamp assembly mounted on the frame for supporting the material and for applying a clamping force to clamp the material against the tester head assembly prior to application of the predetermined measuring forces. The tester head assembly may include a housing; a penetrator assembly carried by the housing, including an axially reciprocal penetrator shaft at the lower end of which is a ball member for contact with the material; an operating assembly for applying a first predetermined force and a second and greater predetermined force to the penetrator shaft for indentation of the material by the ball member, and indicating devices for measuring the difference of indentations of the material by the first and second predetermined forces. A load cell may be attached to the penetrator shaft for measuring the first and second predetermined forces, for controlling the operating assembly by which the first and second predetermined forces are applied to the penetrator shaft, and for reporting load to the control panel.

12 Claims, 3 Drawing Figures

APPARATUS FOR MEASURING THE HARDNESS PROPERTIES OF MATERIALS

BACKGROUND OF THE INVENTION

1. Field of the Invention

The present invention pertains to apparatus for measuring the hardness properties of materials. Specifically, the present invention pertains to improved apparatus for measuring the hardness of metallic materials in accordance with standard Brinell hardness tests.

2. Brief Description of the Prior Art

It is often desired to determine certain physical properties and characteristics of materials. This is particularly true in the production and treatment of metal goods where a particular range of properties, such as hardness, may be desired, specified or required. Hardness, as generally applied to the physical properties of materials such as metals, can be measured by determining resistance to penetration. Several scales or standards of reference for hardness of materials have been developed over the years. Two of the most common scales or tests are the Rockwell Hardness Test and the Brinell Hardness Test.

In the Brinell Hardness Test, a testing machine is provided capable of forcing a ball penetrator, of a specified hardness and diameter, against the material to be tested. Generally, in an instrument measuring depth of the impression, the material is first clamped against the testing machine with a force in excess of the loads to be applied to the ball during the test. During clamping, the penetrator ball is recessed and out of contact with the material. Clamping, by predeforming the specimen area, eliminates distortion or movement of the material during the test.

After the material is properly clamped, a preliminary or set load or force is applied to the penetrator ball. Then a full load or force is applied to the penetrator ball. The load or force applied is dependent upon the ball diameter and the Brinell scales called for in the tests. Then, the test load is reduced to the set load force and the depth of the impression made by the penetrator ball is measured by means of a direct reading device. In a standard Brinell machine, the diameter of the compression, which corresponds to a standard Brinell hardness number, is read with a microscope.

Since there is a mathematical relationship between maximum diameter of the impression made by the penetrator ball and the depth of penetration, depth measuring devices, such as dial indicators, may also be used for determining the sizes of the impressions. In recent years, LVDT's (linear voltage differential transducers) have also been utilized in measuring the depth of penetration. LVDT's provide a stator surrounding an armature which is reciprocal therein along a central axis. The axial or linear position of the armature produces a voltage which is indicative of such position. When used with a hardness tester, the stator of the LVDT is generally fixed or attached to the housing of the tester machine. One end of the LVDT armature is attached to the upper end of a shaft or other component, at the opposite end of which the penetrator ball is carried. Thus, the axial or linear position of the LVDT armature corresponds to the amount of penetration of the material being tested by the penetrator ball. If a differential voltage is obtained between the voltage produced on preliminary load application and the voltage obtained on the full load application, the depth of penetration can be determined. From the depth of penetration the diameter of the recess may be calculated and correlated with the appropriate Brinell hardness number. A Brinell hardness tester utilizing an LVDT is manufactured by the Wilson Instrument Division of American Chain & Cable Company, Inc.

There are number of problems associated with some of the Brinell hardness testing machines of the prior art. For one thing, the clamping force by which the material to be tested is clamped against the tester head may vary due to the weight of the particular part or material being tested. This may result in unaccounted for variations in test results. Due to temperature, friction, pressure surges in fluids by which loads are applied to the penetrator ball, etc., the preliminary or set and full loads applied to the penetrator ball may vary slightly, also resulting in unaccounted for test variations. Furthermore, in tester machines utilizing LVDT's, unaccounted for variations may occur due to the sensitivity of the LVDT's to improper alignment of the armature. If the penetrator shaft or other member to which the LVDT is attached is not stabilized and held in precise coaxial alignment, the voltage differentials produced by the LVDT will not be accurate.

A number of Brinell hardness testing machines have been developed over the years. Some of these machines are capable of making rapid hardness tests required in production line testing. However, for reasons such as those enumerated above, some of these testing machines are not totally acceptable and are not as precise and accurate as would be desired. Thus, attempts continue to be made to produce the desired test results, particularly in production-line testing.

SUMMARY OF THE PRESENT INVENTION

In the present invention, improved apparatus is provided for measuring the Brinell hardness properties of metallic materials which is particularly suitable for fast production-line testing. The apparatus may comprise a frame for supporting the apparatus and the material to be tested; a tester head assembly mounted on the frame for applying predetermined measured forces to the material and a clamp assembly mounted on the frame and supporting the material and applying a clamping force to clamp the material against the tester head assembly prior to the application of the predetermined measured forces. The tester head assembly includes a housing; a penetrator assembly carried by the housing and including an axially reciprocal penetrator shaft at the lower end of which is a ball member for contact with the material; operating means for applying a first predetermined force and a second and greater predetermined force to the penetrator shaft for indentation of the material by the ball member; and means for measuring the difference of indentation of the material by the first and second predetermined forces.

One feature of the apparatus of the present invention is the attachment of a load cell to the penetrator shaft for measuring the first and second predetermined forces and which may be connected to control means for controlling the operating means so as to accurately apply the first and second predetermined forces. By reporting the load applied to the penetrator shaft and controlling from this reading, all factors affecting the accuracy (such as temperature, fluid pressure surges, friction, etc.) are automatically compensated. In addition, this permits variable Brinell loads to be applied through the control means.

The tester head assembly of the present invention also includes a clamping sub attached to the lower end of the housing which includes an annular load cell, the axis of which coincides with the axis of the penetrator shaft which extends therethrough. Upon application of a clamping force to clamp the material to be tested against the tester head, such force is transmitted to the annular load cell, automatically taring out the weight of the part or material being tested, and producing an electrical signal directly proportional to the clamping force being applied. By thus measuring the clamping force and providing an electronic signal thereof, a confirming signal is provided by which the clamping force can be accurately controlled. This also allows varying clamping forces to be selected for different Brinell loads and test specimens and assures that no permanent deformation is applied to the material being tested.

The testing apparatus of the present invention also utilizes an LVDT, responsive to the movement of its penetrator shaft by the first and second predetermined forces, to provide electrical signals representative of the hardness of the material. The armature of the LVDT is attached to an indicator post which is in turn attached to the penetrator shaft of the tester head assembly. The indicator post is uniquely mounted and surrounded by a bearing assembly for radial support and maintaining axial alignment thereof to prevent errors which are present in hardness testing machines of the prior art.

Due to the above-mentioned features and characteristics of the hardness testing apparatus of the present invention, rapid on-line production testing can be performed with a degree of accuracy not permissible with testing machines of the prior art. With the accuracy and control features of the testing apparatus of the present invention there is a minimum of production delay without sacrificing accuracy. Many other objects and advantages of the invention will be apparent from reading the specification which follows in conjunction with the accompanying drawings.

DESCRIPTION OF A PREFERRED EMBODIMENT

Figure 1:
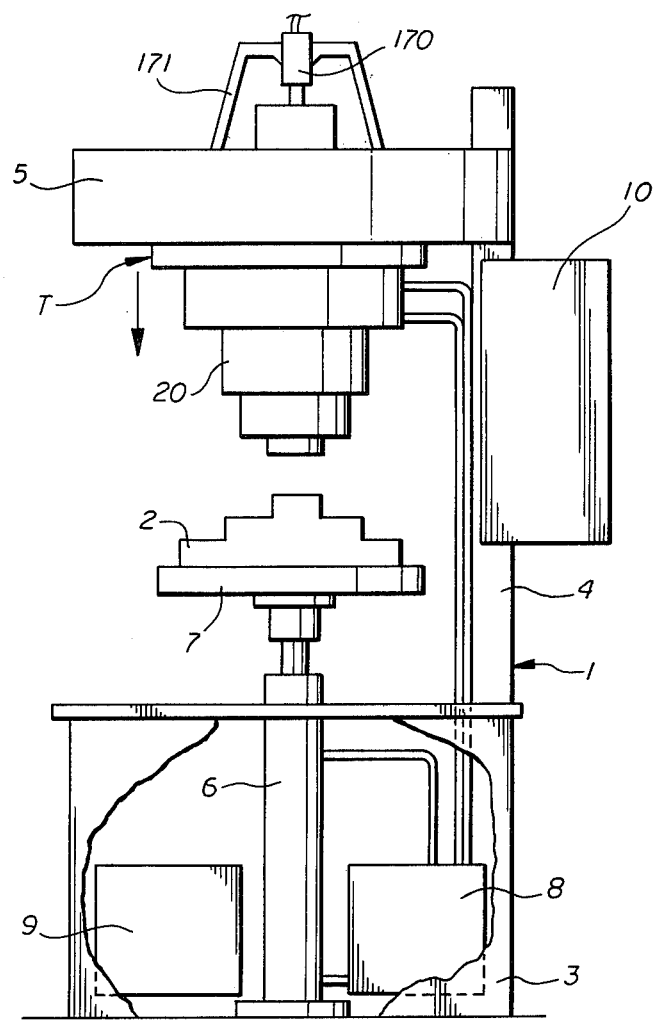
FIG. 1 is an elevation view of apparatus for measuring the hardness properties of materials, according to a preferred embodiment of the invention.
Figure 2:
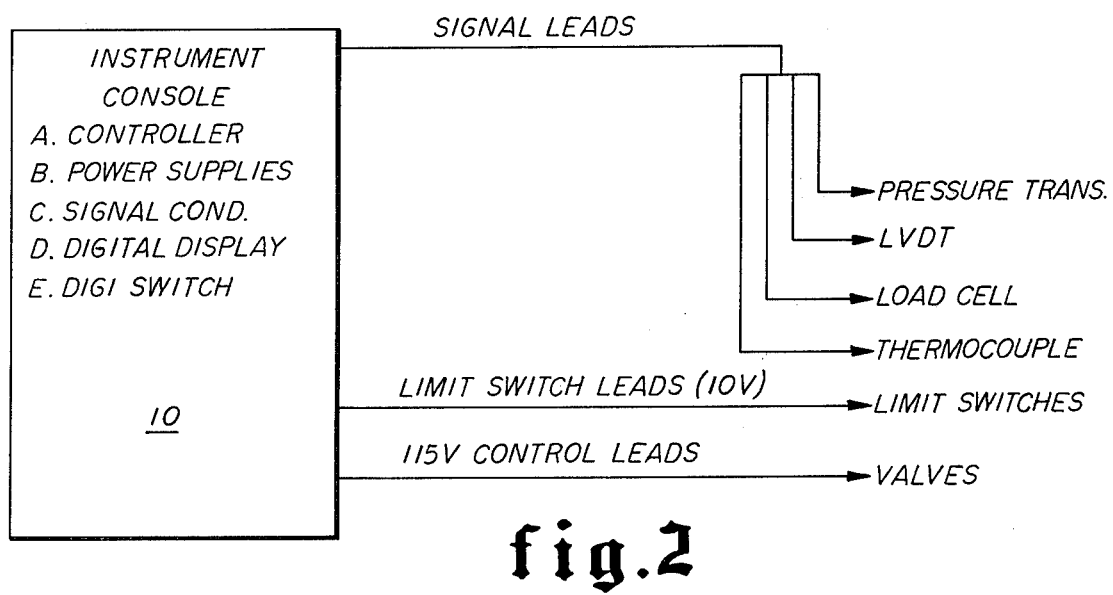
FIG. 2 is a schematic representation of the hardness measuring apparatus of the present invention, particularly for illustrating control circuits thereof.

Referring first to FIG. 1, there is shown apparatus for measuring the hardness properties of materials, according to a preferred embodiment of the invention. The apparatus includes a frame 1 for supporting the apparatus and for supporting the parts or materials 2 to be tested. The frame may be made in any suitable fashion. The one illustrated is a C-type frame which permits production line testing of materials by introducing the material through the open side thereof. The C-frame 1 may include a base section 3, a support column 4 and a cantilevered upper section 5. If desired, the upper section 5 can be mounted on the support column 4 in such a manner as to allow at least some degree of vertical positioning relative to the base section 3. Mounted in the base section 3 is a clamping piston and cylinder assembly 6 surmounted on which is a clamping piston and cylinder assembly 6 surmounted on which is a table 7 or other component on which the parts or materials 2 to be tested may be placed. Mounted on the upper section 5 of the frame 1 is a tester head assembly T for applying predetermined measuring forces to the test material 2 for measuring the hardness properties thereof (in the exemplary embodiment, the Brinell hardness number). The base section 3 of the frame 1 may contain an air compressor 8 or other source of fluid pressure, such as hydraulic pump, for supplying fluid pressure to the clamping piston and cylinder 6 and to the tester head assembly T, as will be more fully understood hereafter. Other components such as an electrical power source 9 could be located in the base section 3. A cabinet and associated panel or console 10 may be attached to the frame 1 for containing various electrical and fluid circuit control elements as well as readout instruments. FIG. 2 is a schematic representation of the various components of console 10 and the control circuits emanating therefrom.

The tester head assembly T of the present invention is unique and will be described in detail hereafter with particular reference to FIG. 3. For initial purposes, it is sufficient to understand that the tester head assembly T includes housing means 20 attached to the upper section 5 of the frame 1. A penetrator assembly is carried by the housing and includes an axially reciprocal penetrator shaft at the lower end of which is a ball member for contact with the test material 2.

After the material 2 is placed on the test table 7, fluid pressure is supplied to the clamping piston and cylinder assembly 6 causing the test material 2 to be clamped against the tester head assembly T with a force greater than the force to be applied to the test material 2 by the tester assembly T during testing. Such clamping eliminates movement or distortion of the material during testing, preventing inaccurate readings resulting therefrom. However, the force should not be so great as to permanently deform the test material 2.

After the material 2 is properly clamped against the tester head assembly T, fluid pressure is applied to an operating portion of the tester head assembly T for applying a first predetermined force and subsequently a second and greater predetermined force to the penetrator shaft of the tester head assembly T for indention of the test material 2 by the ball member on the end of the penetrator shaft. The tester head assembly T is provided with means for measuring the difference of indentation of material and the control panel is provided with means, such as a computer, for converting this measurement to a Brinell hardness number.

Figure 3:
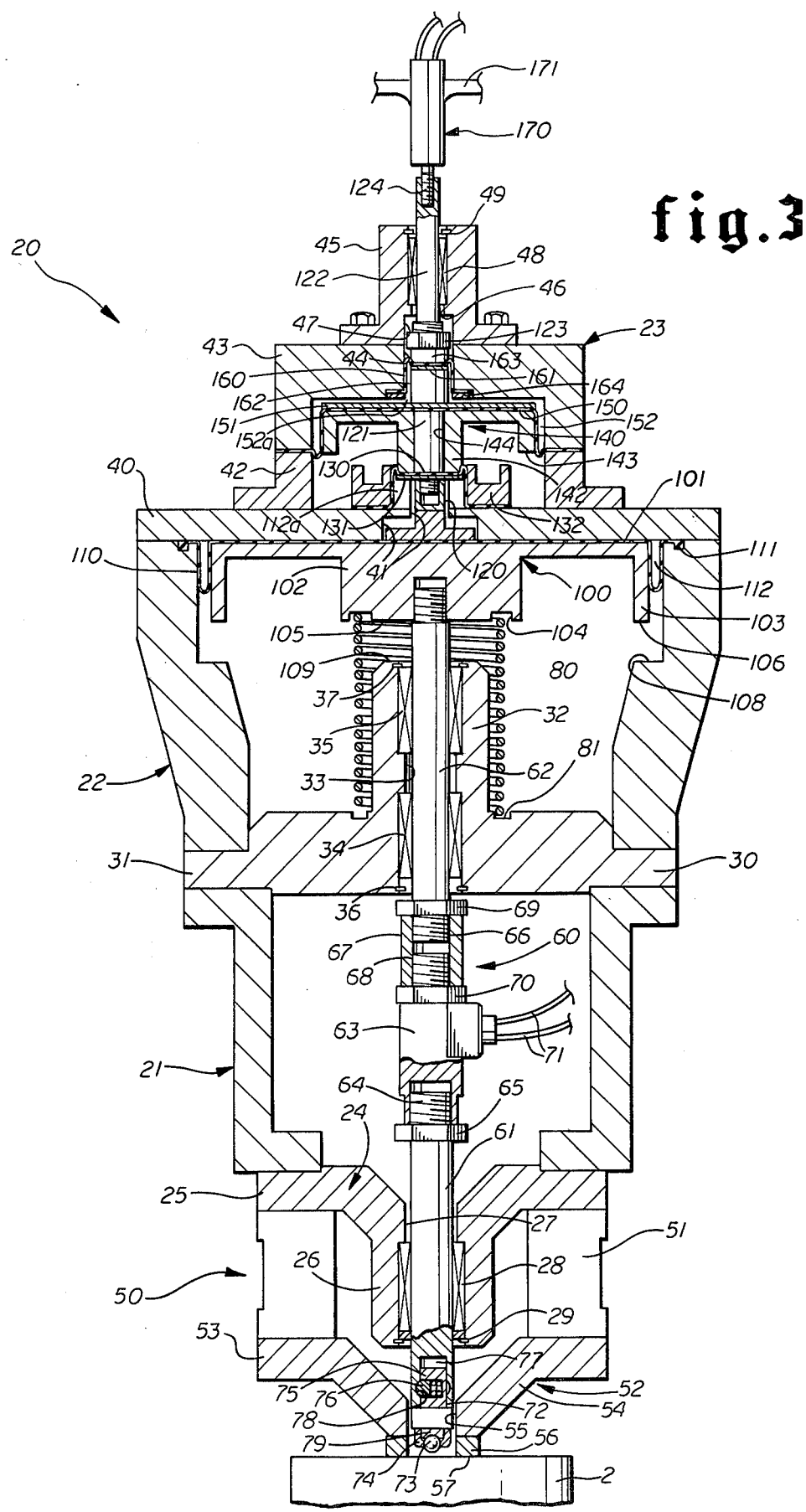
FIG. 3 is an elevation view, partially in section of the tester head assembly of the present invention, according to a preferred embodiment thereof.

Referring now to FIG. 3, the tester head assembly T will be described in greater detail. The housing means 20 includes a lower housing portion 21, an intermediate housing portion 22 and an upper housing portion 23. The lower end of the lower housing portion 21 is closed by a nose member 24 which has a flange portion 25 and a hub portion 26 through which is provided a central aperture 27. Mounted in a counterbored area of the aperture 27 is a linear bearing assembly 28. A snap ring 29 may be provided to hold the bearing assembly 28 in place.

The lower and intermediate housing portions 21 and 22 are separated by a lower plate member 30 which includes on its outer periphery a flange portion 31 and at the center thereof an upwardly projecting hub portion 32 having a central aperture 33 therein. The aperture 33 is counterbored at its lower and upper ends to receive linear bearing assemblies 34 and 35. Snap rings 36 and 37 may be provided to assure that the bearing assemblies 34 and 35 stay in place.

The intermediate and upper housing portions 22 and 23 are separated by an upper plate member 40 having a two-step central aperture 41 therein. The upper housing portion 23 may include a flanged base portion 42 for connection to the plate member 40 and a head portion 43 through which is provided a central aperture 44. The upper end of the upper housing portion 23 is closed by a cap member 45 which is also provided with a central aperture 46. The aperture 46 is counterbored at 47 to a diameter corresponding with the aperture 44 of the head portion 43. The aperture 46 is also counterbored to receive a linear bearing assembly 48 which may be held in place by snap ring 49.

Attached to the lower end of the housing assembly 20 is a clamping sub 50 which includes an annular load cell 51 and a clamping member 52. The clamping member 52 may be provided with a flange portion 53 and a tapered nose portion 54 through which is provided a central aperture 55. A hardened annular wear plate or anvil 56 may be attached to the end of the nose portion 54 providing around the aperture 55 a flat transverse surface against which materials to be tested may be clamped. The various components of the clamping sub 50 and the housing assembly 20 are held together by various bolts, studs, etc. located in radial holes provided therefor.

Centrally disposed within the housing 20 for axial reciprocation therein is a penetrator assembly 60 which includes a penetrator shaft comprising a first shaft portion 61 and a second shaft portion 62 connected by an electronic load cell 63 therebetween. The lower portion 61 of the penetrator shaft may be threadedly connected to the load cell 63 at 64, the connection being maintained by lock nut 65. As illustrated, the upper portion 62 of the penetrator shaft is threadedly connected at 66 to a coupling 67 which is in turn threadedly connected at 68 to the load cell 63. Lock nuts 69 and 70 help maintain these connections. Electrical wires 71 connect the load cell 63 to other components of the electrical circuitry of the measuring apparatus.

The lower end of the penetrator shaft is radially supported and maintained in axial alignment by bearing assembly 28. However, the tolerances between the bearing assembly 28 and lower shaft portion 61 are such as to allow reciprocation of the penetrator shaft within the housing 20. Attached to the lower end of the penetrator shaft is a ball assembly which includes a ball seat 72, a hardened ball 73 and a ball holder or cap 74. The ball seat 72 may be provided with a cylindrical shank 75 in which is mounted a spring loaded pin or ball plunger 76 whose axis is perpendicular to the axis of the penetrator shaft. A corresponding cylindrical recess 77 is provided in the lower end of lower shaft member 61 and an annular groove 78 cut therein. The ball seat member 72 is held in place by engagement of the plunger member 76 with the annular groove 78. The end of the seat member 72 is provided with a spherical recess for engagement by the ball 73. The ball holder or cap 74 is internally threaded for attachment at 79 with external threads on the seat member 72. This arrangement allows easy removal of the ball assembly for replacement of the ball 73 or other components without disturbing any other portion of the tester head assembly. It will be noted that in the initial or inactive position illustrated in FIG. 3, the ball 73 is totally recessed within aperture 55.

The second or upper shaft portion 62 of the penetrator shaft extends upwardly through aperture 33 and the bearing assemblies 34 and 35 mounted therein for threaded connection with a piston member 100. Thus, the upper end of the penetrator shaft is radially supported and maintained in axial alignment by the bearing assemblies 34 and 35. Yet the tolerance is such as to allow reciprocation of the penetrator shaft within the housing 20.

The piston member 100 has a flat circular upper surface 101, a downwardly projecting central hub portion 102 and a peripheral cylindrical skirt 103. An annular groove 104 is provided in the hub portion 102 to receive one end of a return spring 80. The opposite end of the return spring 80 is received in an annular groove 81 provided in the plate member 30. The return spring 80 surrounds the hub portion 32 of the plate member 30 and may be axially compressed therearound. Placed across the piston member 100 is a rolling diaphragm 110. The peripheral edges 111 of the rolling diaphragm 110 are received within an annular groove provided in the upper end of intermediate housing portion 22 and held in place by engagement of the upper plate member 40. A variable volume fluid chamber 112 is defined by the lower surface of the upper plate member 40 and the upper surface of the rolling diaphragm 110. This fluid chamber 112 may communicate with a source of fluid pressure through a port (not shown) in the upper plate member 40. Thus, it will be understood that upon the introduction of enough fluid pressure into the variable chamber 112, the piston member 100 and the attached penetrator shaft may be axially displaced, in a downwardly direction as viewed in FIG. 3.

To limit the downwardly axial movement of the piston 100 and the penetrator assembly 60, an upwardly facing annular shoulder 108 is provided around the inner periphery of the intermediate housing portion 22. It will also be noted that an upwardly facing annular shoulder 109 is provided on the upper end of the lower plate member hub portion 42. On downwardly movement of the piston member 100, the downwardly facing surface 105 of the hub portion 102 and the downwardly facing annular surface 106 on the skirt portion 103 will simultaneously engage annular shoulders 109 and 108, respectively arresting movement of the piston member 100 and the penetrator assembly 60 attached thereto.

Centrally affixed to the upper side of piston 100 for disposal within the aperture region 41 of upper plate member 40 is a post base 120 which is internally threaded to receive a correspondingly threaded lower portion 121 of an indicator post or shaft, a smaller diameter upper portion 122 of which is connected thereto by a threaded collar 123.

Directly disposed underneath the shoulder of the lower indicator post portion 121 is a rolling diaphragm seal 130 and seal plate 131. The diaphragm 130 and seal plate 131 have central holes through which the threaded end of the indicator post portion 121 extends for threaded connection with the post base 120. It will also be noted that the rolling diaphragm seal 130 is engaged by the lower surface of the hub portion 142 of an upper piston member 140 which, like the piston member 100 is also provided with a cylindrical skirt 143. The outer periphery of the rolling diaphragm seal 130 is attached to the upper plate member 40 and held in place by an annular retainer ring 132. It will be noted that the annular space 112a surrounding the post base 120 is in fluid communication with and forms a part of the variable volume fluid chamber 112, the diaphragm seal 130 serving as the upper seal for such fluid chamber.

The upper piston member 140 is provided with a central aperture 144 through which the lower indicator post portion 121 extends. The piston member 140 is centrally disposed within the upper housing portion 23 for axial reciprocation therein. Extending across the upper surface of the piston member 140 is another diaphragm member 150 the peripheral edges of which are held in place between base member 42 and head member 43. A circular plate 151 may be utilized to hold the diaphragm 150 tightly against piston member 140. Thus, another variable volume fluid chamber 152 is provided between the diaphragm 150 and the lower surfaces of the head portion 43 of the upper housing portion 23. This fluid chamber 152 is sealed at the upper end thereof by another diaphragm 160 the central portion of which is held in place by a diaphragm plate or washer 161 on opposite sides of which are cylindrical collars 162 and 163. The outer periphery of diaphragm seal 160 is held in place by an annular retainer ring 164. The annular space 152a surrounding the collar 162 communicates with and forms a portion of the variable volume fluid chamber 152.

The upper indicator post portion 122 is centrally disposed within apertures 47 and 46 and the bearing assembly 48 for reciprocal movement therein. The bearing assembly 48 radially supports and maintains axial alignment of the indicator post 121, 122 upon reciprocal movement thereof. From the foregoing description of the penetrator shaft assembly 60, piston members 100, 140 and the components surmounted thereon, it can easily be understood that these assemblies are simultaneously reciprocal as an integral unit within the housing 20.

It will be noted that the upper end of the indicator post 122 is drilled and threaded 124 for threadedly receiving one end of the armature of an LVDT (linear voltage differential transducer) 170. The LVDT is a transducer which produces a voltage signal dependent upon the linear or axial position of its armature relative to a stator or stationary portion of the LVDT. Thus, if the stator of the LVDT is stationarily fixed, by support members 171 or the like, relative to the housing assembly 20 of the tester head, and the armature of the LVDT coaxially affixed to the indicator post 122, the relative axial position of the penetrator shaft 60 (which moves integrally with the indicator post 122) will correspond with a particular voltage signal produced by the LVDT. As will be understood hereafter, this relationship will allow the determination of hardness of the material being tested by the apparatus.

As already pointed out, the test head assembly of the present invention is provided with a first or upper piston member 140 and a second or lower piston member 100. Each of these pistons members is associated with a fluid chamber 152, 112 which is in turn connected to a source of fluid pressure. These piston members 140, 100, the source of fluid pressure and the means for controlling pressure are portions of the operating means by which predetermined forces may be applied to the penetrator shaft 60 for indentation of the materials being tested by the ball member 73. Since the first or upper piston member 140 is substantially smaller than the second or lower piston member 100, a smaller force is generated thereby. Thus, the first piston member 140 is primarily for providing a first predetermined setting force. The larger piston member 100 is for providing the second and greater predetermined full load force on the penetrator shaft 60.

STATEMENT OF OPERATION

Referring now to all of the drawings, operation of the improved apparatus of the present invention for measuring the hardness properties of materials will be explained. The material 2 is placed on the clamping assembly 6 and 7 of the apparatus and a predetermined pressure applied to the piston and cylinder 6 so that the material 2 is clamped against the tester head assembly T with a predetermined force. As this is done the penetrator shaft 60 is in the retracted or recessed position shown in FIG. 3. The test material 2 contacts and is pressed against the flat surface 57 of the anvil member 56. This force is also transmitted to the load cell 51 producing a signal representative of the clamping force. As already indicated, the weight of the test material 2 is automatically tared from this measurement. The signal from the load cell 51 can be transmitted to various control components located in the control console or panel 10 to control the amount of pressure applied to the piston and cylinder assembly 6, thus controlling the clamping force. A digital readout device might also be provided at the panel 10 so that the clamping force may be visually confirmed.

After the proper clamping force is applied to the test material 2 and tester head assembly T, a setting pressure is introduced to the variable fluid chamber 152 and the piston member 140 causing the penetrator shaft 60 to move downwardly for contact of the ball member 73 with the test material 2 under a first predetermined force. This first predetermined force is measured by the load cell 63 and transmitted through lead wire 71 to a readout device for confirmation of the force and if desired to control devices in the control panel for controlling or adjusting the fluid pressure in the chamber 152 to a precise value for the first predetermined force (preliminary or set load). This force is primarily to take out any slack in the parts of the tester head assembly T and to slightly penetrate the test material to reduce the effect of surface finish on hardness measurements.

As soon as the preliminary or set load is applied to the test material, the voltage signal generated at the LVDT 170 attached to the indicator post 122 is measured and recorded. In fact, a computer device may be utilized for receiving such a signal and storing it for future use. The predetermined fluid pressure is applied to the fluid chamber 112 of the operating assembly causing a second and greater predetermined force to be generated by piston member 100 for application to the penetrator shaft 60 and ball member 73 at the lower end thereof. This force is again measured and verified by the load cell 63, the signal of which is transmitted through lead line 71 to read out devices, and if desired, control devices located in the control panel 10. If the force is not precisely as desired, the fluid pressure can be adjusted by these control devices.

Application of the second and greater predetermined force (full load) to the ball member 73 results in further indentation of the test material 2. Further indentation of the test material, of course, causes the penetrator shaft 60 and indicator post 122 to be axially displaced. Axial displacement of these members results in axial displacement of the armature of the LVDT 170 resulting in a signal therefrom indicative of such displacement. This signal is transmitted to readout devices or to a computer and the difference in voltage signals generated from the set load and the full load determined. This difference is, of course, indicative of the amount of axial displacement of the penetrator shaft 60 between the set load and the full load. The amount of axial displacement is in turn indicative of the hardness of the material being tested. Since there is a mathematical relationship between the depth of penetration of the ball 73 into the test material and the diameter of the recess produced thereby, this diameter can be mathematically determined and correlated with the Brinell hardness number indicative of the hardness of the material. These calculations can be made quickly by a computer to which the LVDT would be attached. As soon as the calculations have been made and recorded, pressure can be relieved from the fluid chambers 112 and 152, return spring 80 causing the piston member 140, 100, the penetrator shaft 60, and the indicator post 122 to return to the initial or inoperative position indicated in FIG. 3. The test can then be repeated on the next material to be tested.

Thus, the present invention provides improved apparatus for measuring the hardness properties of material utilizing several unique features. One unique feature is the provision of a load cell to measure the initial clamping force applied to the test material in the tester head assembly. This automatically tares out the weight of the test material, insuring that proper clamping force is applied. By measuring the clamping force electronically, a confirming signal can be reported to a control panel and if desired, used to select clamping forces for different Brinell loads and specimen weights, assuring that no permanent damage or deformation of the test material results.

Another unique feature is the provision of a load cell in the penetrator shaft by which the first and second predetermined forces applied to the penetrator shaft can be monitored and axially controlled. By reporting these loads and controlling from such reported readings, factors affecting accuracy such as temperature, varying forces of the piston return spring, fluid pressure surges, friction, etc. may be automatically compensated. In addition, different loads for different Brinell tests may be applied and controlled by computing the voltage output from the load cell for a given load.

The manner of supporting and maintaining axial alignment of the penetrator shaft and the indicator post to which the LVDT is attached is also unique. The arrangement of these bearing assemblies results in much greater accuracy than testers of the prior art which utilize LVDT's.

While a single embodiment of the invention has been described herein, many variations can be made by those skilled in the art, without departing from the spirit of the invention. Accordingly, it is intended that the scope of the invention be limited only by the claims which follow.

I claim:

1. Improved apparatus for measuring the hardness properties of materials comprising a frame for supporting said apparatus and the material to be tested; a tester head assembly mounted on said frame for applying predetermined measuring forces to said material and a clamp assembly mounted on said frame for supporting said material and for applying a clamping force to clamp said material against said tester head assembly prior to said application of said predetermined measuring forces; said tester head assembly including housing means attached to said frame; a penetrator assembly carried by said housing, including an axially reciprocal penetrator shaft at the lower end of which is a penetrator member for contact with said material; operating means for applying a first predetermined force and a second and greater predetermined force to said penetrator shaft for indentation of said material by said penetrator member and means for measuring the difference of indentation of said material by said first and second predetermined forces; wherein the improvement comprises:

an electronic load cell for measuring said first and second predetermined forces attached between and connecting a first shaft portion, being the lower end of said penetrator shaft, and a second shaft portion, being the upper end of said penetrator shaft; said housing means comprising a lower housing portion in which said penetrator shaft is carried, an intermediate housing portion and an upper housing portion, said operating means including first and second piston members carried in said upper and intermediate housing portions, respectively, and responsive to fluid pressures applied thereto for applying said first and second predetermined forces to said penetrator shaft.

2. Improved measuring apparatus as set forth in claim 1 in which said load cell is connected to a readout device for visual confirmation of said first and second predetermined forces.

3. Improved measuring apparatus as set forth in claim 1 in which said load cell is connected to control devices for controlling said operating means for precisely applying said first and second predetermined forces.

4. Improved measuring apparatus as set forth in claim 1 in which said penetrator member comprises a ball assembly which includes a hardened ball attached to a ball seat, said ball seat having a cylindrical shank received by a corresponding cylindrical recess at the lower end of said first shaft portion, said ball seat being disengageable from said first shaft portion for replacement of said ball without disturbing any other portion of said measuring apparatus.

5. Improved measuring apparatus as set forth in claim 1 in which said lower and intermediate housing portions are separated by a lower plate member having a central aperture therein through which said penetrator shaft projects for attachment to said second piston member and in which is disposed at least one bearing member for radially supporting and maintaining axial alignment of said penetrator shaft upon reciprocation thereof, the lower end of said lower housing being closed by a nose member having a central aperture therein through which said penetrator shaft projects for said contact of said penetrator member with said material and in which is disposed at least one bearing member for radially supporting and maintaining axial alignment of said penetrator shaft upon said reciprocation thereof.

6. Improved measuring apparatus as set forth in claim 5 in which said lower plate member comprises an upwardly projecting hub portion providing a first upwardly facing annular shoulder thereon surrounding said penetrator shaft and in which said intermediate housing portion is provided with a second upwardly facing annular shoulder around the inner periphery thereof, said first and second annular shoulders being simultaneously engageable with the central and outer portions, respectively, of said second piston member to limit the downward movement of said second piston member and penetrator shaft by operating means.

7. Improved measuring apparatus as set forth in claim 5 in which said intermediate and upper housing portions are separated by an upper plate member having a central aperture therein through which said first and second piston members are connected for simultaneous movement with said penetrator shaft.

8. Improved measuring apparatus as set forth in claim 7 in which the upper end of said upper housing portion is closed by a cap member having a central aperture therein through which an indicator post centrally connected to said first piston member projects for reciprocal movement with said first and second piston members and said penetrator assembly, said indicator post being a portion of said means for measuring the difference of indentation of said material by said first and second predetermined forces.

9. Improved measuring apparatus as set forth in claim 8 in which said means for measuring the difference of indentation of said material comprises an LVDT (linear voltage differential transducer) the stator of which is stationarily fixed relative to said housing means and the armature of which is coaxially aligned with and attached to the upper end of said indicator post, said LVDT being responsive to the movement of said penetrator shaft by said first and second predetermined forces to provide electrical signals representative of the hardness of said material.

10. Improved measuring apparatus as set forth in claim 9 including a bearing assembly attached to said cap member surrounding, radially supporting and maintaining axial alignment of said indicator post upon said reciprocal movement thereof.

11. Improved measuring apparatus as set forth in claim 5 in which said tester head assembly includes a clamping sub attached to the lower end of said housing means and having a central aperture in which the lower end of said penetrator shaft is freely disposed and around which is provided a flat transverse surface against which said material may be clamped by application of said clamping forces, said clamping sub including an annular load cell, the axis of which coincides with the axis of said penetrator shaft, said annular load cell providing electrical signals representative of said clamping force.

12. Improved measuring apparatus as set forth in claim 11 in which said annular load cell is connected to a readout device for visual confirmation of said clamping force.

* * * * *